United States Patent [19]

Gates et al.

[11] 4,162,154
[45] Jul. 24, 1979

[54] HERBICIDALLY-ACTIVE SULPHONATES

[75] Inventors: Peter S. Gates; Derek Baldwin, both of Cambridge, England

[73] Assignee: Fisons Limited, London, England

[21] Appl. No.: 875,189

[22] Filed: Feb. 3, 1978

[30] Foreign Application Priority Data

| Feb. 5, 1977 | [GB] | United Kingdom | 4847/77 |
| Feb. 5, 1977 | [GB] | United Kingdom | 4848/77 |
| Feb. 5, 1977 | [GB] | United Kingdom | 4849/77 |
| Aug. 5, 1977 | [GB] | United Kingdom | 32839/77 |

[51] Int. Cl.² ............... A01N 9/14; C07D 307/79; C07D 307/86
[52] U.S. Cl. ............... 71/88; 260/327 B; 260/340.2; 260/340.3; 260/346.22; 260/346.71; 260/346.73; 260/456 P; 260/456 A; 71/86; 71/87; 71/90; 71/103
[58] Field of Search .......... 260/346.22, 346.73; 71/88

[56] References Cited

U.S. PATENT DOCUMENTS

| 2,318,895 | 5/1943 | Smith | 260/346.22 |
| 3,946,048 | 3/1976 | Fischer et al. | 260/346.73 |
| 4,051,154 | 9/1977 | Gates et al. | 260/346.22 |

*Primary Examiner*—Natalie Trousof
*Assistant Examiner*—Bernard Dentz
*Attorney, Agent, or Firm*—Wenderoth, Lind & Ponack

[57] ABSTRACT

The invention provides herbicidally-active sulphonates of the formula

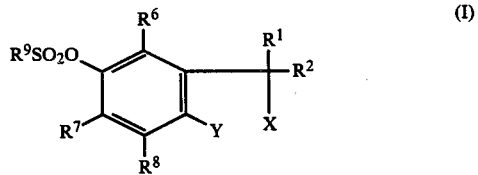

(I)

wherein X represents a group —CHR³—OR⁴ and Y represents a group —OR⁵, or X and Y together represent a group —CHR³—O— or a group —CHR³—O—Z—O—, the free oxygen atom of which is attached to the benzene ring; $R^1$, $R^2$ and $R^3$, which may be the same or different, each represent hydrogen or C 1 to 6 alkyl, or $R^1$ and $R^2$ together or $R^2$ and $R^3$ together form a C 3 to 6 alkylene chain; $R^4$ and $R^5$, which may be the same or different, each represent hydrogen, C 1 to 6 alkyl, C 2 to 6 alkenyl, C 2 to 6 alkynyl, phenyl, a group —O(=O)$R^{10}$ or a group —SO$_2$$R^{11}$; $R^6$, $R^7$ and $R^8$, which may be the same or different, each represent hydrogen, C 1 to 6 alkyl, halogen, cyano, C 2 to 6 carboxylic acyl, or C 1 to 4 alkoxy; $R^9$ represents C 1 to 6 alkyl, phenyl or C 7 to 10 phenylalkyl (each of which may be unsubstituted or substituted by one or more chlorine or bromine atoms, C 1 to 4 alkyl groups, C 1 to 4 alkoxy groups or nitro groups), C 5 to 7 cycloalkyl, C 1 to 4 alkylamino, or dialkylamino wherein each alkyl moiety has from 1 to 4 carbon atoms; $R^{10}$ represents C 1 to 6 alkyl or alkoxy, C 2 to 6 alkenyl or alkenyloxy, C 2 to 6 alkynyl or alkynyloxy, phenyl, phenoxy, phenylamino, C 1 to alkylamino alylamino or dialkylamino wherein each alkyl moiety has from 1 to 6 carbon atoms, each of the groups which $R^{10}$ may represent being unsubstituted or substituted by one or more halogen atoms or C 1 to 4 alkoxy groups; $R^{11}$ represents C 1 to 6 alkyl, phenyl, C 1 to 6 alkylamino or dialkylamino each of the alkyl moieties thereof having from 1 to 6 carbon atoms, each of the groups which $R^{11}$ may represent being unsubstituted or substituted by one or more halogen atoms or C 1 to 4 alkoxy groups; Z represents a group of formula —S(=O)n, —C$R^{12}$$R^{13}$ or —P(=Q)(O$R^{14}$)—; n represents 1 or 2; $R^{12}$ and $R^{13}$, which may be the same or different, each represent hydrogen, C 1 to 6 alkyl or alkoxy, C 2 to 6 alkenyl or alkynyl, phenyl, phenoxy, cyano or (C 1 to 6 alkoxy)carbonyl, or $R^{12}$ and $R^{13}$ together represent an oxygen atom, a sulphur atom, a C 3 to 6 alkylene chain or a C 1 to 6 alkylimino group or a phenylimino group; and $R^{14}$ represents C 1 to 6 alkyl; and Q represents oxygen or sulphur, together with processes for their preparation and herbicidal compositions containing them.

9 Claims, No Drawings

HERBICIDALLY-ACTIVE SULPHONATES

This invention concerns herbicidally active sulphonates, processes for their preparation, and compositions containing them.

In one aspect, this invention provides the sulphonates of the formula:

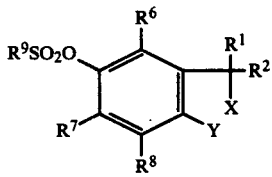

(I)

wherein X represents a group —CHR$^3$—OR$^4$ and Y represents a group —OR$^5$, or X and Y together represent a group —CHR$^3$—O— or —CHR$^3$—O—Z—O—, the free oxygen atom of which is attached to the benzene ring; R$^1$, R$^2$ and R$^3$, which may be the same or different, each represent hydrogen or alkyl, or R$^1$ and R$^2$ together or R$^2$ and R$^3$ together form an alkylene chain; R$^4$ and R$^5$, which may be the same or different, each represent hydrogen, alkyl, alkenyl, alkynyl, aryl, a group C(=O)R$^{10}$ or a group —SO$_2$R$^{11}$; R$^6$, R$^7$ and R$^8$, which may be the same or different, each represent hydrogen, alkyl, halogen, cyano, carboxylic acyl or alkoxy; R$^9$ represents alkyl, aryl or aralkyl (each of which may be substituted or unsubstituted), cycloalkyl, alkylamino or dialkylamino; R$^{10}$ represents alkyl, alkenyl, alkynyl, aryl, alkoxy, alkenyloxy, alkynyloxy, aryloxy, alkylamino, arylamino or dialkylamino (each of which may be substituted or unsubstituted); R$^{11}$ represents alkyl, aryl, alkylamino or dialkylamino (each of which may be substituted or unsubstituted); Z represents a group of formula

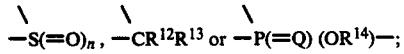

n represents 1 or 2; R$^{12}$ and R$^{13}$, which may be the same or different, each represent hydrogen, alkyl, alkenyl, alkynyl, alkoxy, aryl, aryloxy, cyano or alkoxycarbonyl, or R$^{12}$ and R$^{13}$ together represent an oxygen atom, a sulphur atom, an alkylene chain or an alkylimino or arylimino group; R$^{14}$ represents alkyl; and Q represents oxygen or sulphur.

R$^1$ preferably represents alkyl of 1 to 6 carbon atoms, especially 1 to 4 carbon atoms, for example methyl or ethyl.

R$^2$ preferably represents alkyl of 1 to 6 carbon atoms, especially 1 to 4 carbon atoms, for example methyl or ethyl.

R$^3$ preferably represents hydrogen. When, however, it represents alkyl, it is preferably of 1 to 6 carbon atoms, especially 1 to 4 carbon atoms, for example methyl or ethyl.

When R$^1$ and R$^2$ together or R$^2$ and R$^3$ together represent an alkylene chain, it is preferably of 3 to 6, especially 4 or 5 carbon atoms.

R$^4$ and R$^5$ are preferably the same as each other. When one or both of them represents alkyl it is preferably of 1 to 6 carbon atoms, especially methyl or ethyl. Preferred alkenyl and alkynyl groups which each may represent are of 2 to 6 carbon atoms, for example allyl or propargyl. When one or both of them represents aryl it is preferably phenyl. When one or both of R$^4$ and R$^5$ represents a group C(=O)R$^{10}$ or —SO$_2$R$^{11}$, the group R$^{10}$ or R$^{11}$ is preferably such that any alkyl moiety thereof has from 1 to 6 carbon atoms, especially methyl or ethyl, any alkenyl or alkynyl moiety thereof has from 2 to 6 carbon atoms, especially allyl or propargyl, and any aryl moiety thereof is phenyl. Preferably the group which R$^{10}$ or R$^{11}$ represents is unsubstituted. However, when it represents a substituted group, the substituent(s) thereon are preferably halogen, especially chlorine, or alkoxy, especially of 1 to 4 carbon atoms, for example methoxy.

Specific preferred groups which R$^4$ and/or R$^5$ may represent include hydrogen, methyl, ethyl, allyl, propargyl, phenyl, acetyl, isobutyryl, methylcarbamoyl, chloroacetyl, pentanoyl, benzoyl, ethoxycarbonyl, 4-chloro-2-butynyloxycarbonyl, 2-chloroethoxycarbonyl, methylsulphonyl, benzoyl, methoxycarbonyl, trichloroacetyl, crotonyl and phenylcarbamoyl.

R$^6$, R$^7$ and R$^8$ independently preferably represent hydrogen. When one or more thereof is other than hydrogen, however, it is preferably alkyl of 1 to 6 carbon atoms (e.g. methyl or ethyl), chlorine, bromine, cyano, carboxylic acyl of 2 to 6 carbon atoms (e.g. acetyl) or alkoxy of 1 to 4 carbon atoms (e.g. methoxy or ethoxy).

R$^9$ preferably represents alkyl of 1 to 6 carbon atoms, especially 1 to 4 carbon atoms, which is unsubstituted or substituted by one or more halogen atoms, for example methyl, ethyl, n-propyl, isopropyl, n-butyl, i-butyl or s-butyl (either unsubstituted or substituted by a chlorine or bromine atom). Further preferred values for R$^9$ are phenyl and phenylalkyl of 7 to 10 carbon atoms (especially benzyl), each of which may be unsubstituted or substituted by one or more chlorine or bromine atoms, alkyl or alkoxy groups of 1 to 4 carbon atoms (e.g. methyl or methoxy) or nitro groups, for example 4-chlorophenyl, 4-bromobenzyl, p-tolyl, 2-methoxyphenyl, 3-nitrophenyl or 3,4-dichlorophenyl, and cycloalkyl of 5 to 7 carbon atoms (especially cyclopentyl or cyclohexyl), alkylamino and dialkylamino, especially where the alkyl moieties thereof have from 1 to 4 carbon atoms, e.g. methylamino, ethylamino or dimethylamino.

Z preferably represents a group —CR$^{12}$R$^{13}$ as defined hereinbefore.

When Z represents a group —CR$^{12}$R$^{13}$, the group R$^{12}$ or R$^{13}$ is preferably such that any alkyl moiety thereof has from 1 to 6 carbon atoms, e.g. methyl or ethyl, any alkenyl or alkynyl moiety thereof has from 2 to 6 carbon atoms, especially allyl or propargyl, and any aryl moiety thereof is phenyl. When R$^{12}$ and R$^{13}$ together represent an alkylene chain, it is preferably of from 3 to 6, especially 4 to 5 carbon atoms.

Specific preferred groups R$^{12}$ and R$^{13}$ are hydrogen, methyl, ethyl, n-propyl, isopropyl, chloromethyl, bromomethyl, methoxy, ethoxy, phenyl, tetramethylene and pentamethylene.

When Z represents a group —P(=Q) (OR$^{14}$), R$^{14}$ is preferably of 1 to 6 carbon atoms, for example methyl or ethyl.

A preferred sub-group of compounds within formula I (hereinafter referred to as sub-group A) comprises those compounds wherein X and Y together represent a group —CHR$^3$—O—.

Within sub-group A, in a preferred class of compounds, R$^1$ represents alkyl of 1 to 4 carbon atoms, R$^2$ represents alkyl of 1 to 4 carbon atoms, R$^3$ represents hydrogen or alkyl of 1 to 4 carbon atoms, $R^6$, $R^7$ and $R^8$ each represent hydrogen, and $R^9$ represents methyl, ethyl, n-propyl, isopropyl, n-butyl, isobutyl or s-butyl (each of which is unsubstituted or substituted by a chlorine or bromine atom), phenyl or benzyl (each of which is unsubstituted or substituted by one or more chlorine or bromine atoms or methyl, methoxy or nitro groups), cyclopentyl, cyclohexyl, methylamino, ethylamino or dimethylamino.

A further preferred class within sub-group A comprises those compounds of formula I wherein $R^1$ represents methyl or ethyl, $R^2$ represents methyl or ethyl, $R^3$, $R^6$, $R^7$ and $R^8$ each represent hydrogen, and $R^9$ represents methyl, ethyl, n-propyl, isopropyl, n-butyl, isobutyl, s-butyl, chloromethyl, 3-chloropropyl, phenyl, benzyl, p-tolyl, cyclopentyl, cyclohexyl, methylamino, ethylamino or dimethylamino.

Specific preferred compounds within sub-group A are:

2,3-dihydro-3,3-dimethylbenzofuran-5-yl methanesulphonate,
2,3-dihydro-3,3-dimethylbenzofuran-5-yl ethanesulphonate,
2,3-dihydro-3,3-dimethylbenzofuran-5-yl 1-propanesulphonate,
2,3-dihydro-3,3-dimethylbenzofuran-5-yl 1-butanesulphonate,
2,3-dihydro-3,3-dimethylbenzofuran-5-yl 2-propanesulphonate,
2,3-dihydro-3,3-dimethylbenzofuran-5-yl 2-butanesulphonate,
2,3-dihydro-3,3-dimethylbenzofuran-5-yl 2-methyl-1-propanesulphonate,
2,3-dihydro-3,3-dimethylbenzofuran-5-yl chloromethanesulphonate,
2,3-dihydro-3,3-dimethylbenzofuran-5-yl 3-chloro-1-propanesulphonate,
2,3-dihydro-3,3-dimethylbenzofuran-5-yl cyclohexane sulphonate,
2,3-dihydro-3,3-dimethylbenzofuran-5-yl p-toluenesulphonate,
2,3-dihydro-3,3-dimethylbenzofuran-5-yl α-toluenesulphonate,
2,3-dihydro-3,3-dimethylbenzofuran-5-yl methylsulphamate, and spiro[benzofuran-3(2H),1'-cyclopentan]-5-yl methanesulphonate.

Specific preferred compounds of formula I wherein X and Y together represent a group —CHR³—O—Z—O (hereinafter referred to as sub-group B) are:

4,5-dihydro-5,5-dimethyl-2-oxide-1,3,2-benzodioxathiepin-7-yl methanesulphonate,
4,5-dihydro-2,2,5,5-tetramethyl-1,3-benzodioxepin-7-yl methanesulphonate;
4,5-dihydro-2-methoxy-5,5-dimethyl-1,3-benzodioxepin-7-yl methanesulphonate;
2-ethyl-4,5-dihydro-2,5,5-trimethyl-1,3-benzodioxepin-7-yl methanesulphonate;
2,2-diethyl-4,5-dihydro-5,5-dimethyl-1,3-benzodioxepin-7-yl methanesulphonate;
4,5-dihydro-2-isopropyl-2,5,5-trimethyl-1,3-benzodioxepin-7-yl methanesulphonate;
4,5-dihydro-5,5-dimethyl-1,3-benzodioxepin-7-yl methanesulphonate;
4,5-dihydro-2,5,5-trimethyl-1,3-benzodioxepin-7-yl methanesulphonate;
4,5-dihydro-5,5-dimethyl-2-phenyl-1,3-benzodioxepin-7-yl methanesulphonate;
4,5-dihydro-2,5,5-trimethyl-2-phenyl-1,3-benzodioxepin-7-yl methanesulphonate;
4,5-dihydro-5,5-dimethylspiro[1,3-benzodioxepin-2,1'-cyclohexan]-7-yl methanesulphonate;
4,5-dihydro-5,5-dimethylspiro[1,3-benzodioxepin-2,1'-cyclopentan]-7-yl methanesulphonate;
2-chloromethyl-4,5-dihydro-2,5,5-trimethyl-1,3-benzodioxepin-7-yl methanesulphonate;
2-bromomethyl-4,5-dihydro-5,5-dimethyl-1,3-benzodioxepin-7-yl methanesulphonate;
2-ethoxy-4,5-dihydro-5,5-dimethyl-1,3-benzodioxepin-7-yl methanesulphonate;
2-ethyl-4,5-dihydro-2-methoxy-5,5-dimethyl-1,3-benzodioxepin-7-yl methanesulphonate; and
2-ethoxy-4,5-dihydro-5,5-dimethyl-2-oxo-1,3,2benzodioxaphosphepin-7-yl methanesulphonate.

Specific preferred compounds of formula I wherein X represents —CHR³—OR⁴ and Y represents —OR⁵ (hereinafter referred to as sub-group C) are:

4-hydroxy-3-(2-hydroxy-1,1-dimethylethyl)phenyl methanesulphonate;
4-hydroxy-3-(2-hydroxy-1,1-dimethylethyl)phenyl ethanesulphonate (this compound being particularly preferred);
4-acetoxy-3-(2-acetoxy-1,1-dimethylethyl)phenyl methanesulphonate;
4-isobutyryloxy-3-(2-isobutyryloxy-1,1-dimethylethyl)phenyl methanesulphonate,
4-methylcarbamoyloxy-3-(2-methylcarbamoyloxy-1,1-dimethylethyl)-phenyl methanesulphonate;
4-hydroxy-3-(1-hydroxymethyl)cyclopentyl)phenyl methanesulphonate;
4-hydroxy-3-(1-(hydroxymethyl)cyclohexyl)phenyl methanesulphonate;
4-chloroacetyloxy-3-(2-chloroacetyloxy-1,1-dimethylethyl)phenyl methanesulphonate;
4-pentanoyloxy-3-(2-pentanoyloxy-1,1-dimethylethyl)phenyl methanesulphonate;
4-benzoyloxy-3-(2-benzoyloxy-1,1-dimethylethyl)-phenyl methanesulphonate;
4-(ethoxycarbonyloxy)-3-(2-(ethoxycarbonyloxy)-1,1-dimethylethyl)phenyl methanesulphonate;
4-(4-chloro-2-butynyloxycarbonyloxy)-3-(2-(4-chloro-2-butynyloxycarbonyloxy)-1,1-dimethylethyl)phenyl methanesulphonate;
4-(2-chloroethoxycarbonyloxy)-3-(2-(2-chloroethoxycarbonyloxy)-1,1-dimethylethyl)phenyl methanesulphonate;
4-methanesulphonyloxy-3-(2-methanesulphonyloxy-1,1-dimethylethyl)phenyl methanesulphonate;
3-(2-benzoyloxy-1,1-dimethylethyl)-4-hydroxyphenyl methanesulphonate;
4-methoxycarbonyloxy-3-(2-(methoxycarbonyloxy)-1,1-dimethylethyl)phenyl methanesulphonate;
4-(trichloroacetyloxy)-3-(2-(trichloroacetyloxy)-1,1-dimethylethyl)phenyl methanesulphonate;
4-crotonyloxy-3-(2-crotonyloxy-1,1-dimethylethyl)-phenyl methanesulphonate;
4-(phenylcarbamoyloxy)-3-(2-(phenylcarbamoyloxy)-1,1-dimethylethyl)phenyl methanesulphonate;

The compounds of formula I possess, when $R^3$ is other than hydrogen or $R^1$ and $R^2$ are not identical, at least one asymmetric carbon atom. They may therefore exist as distinct stereoisomeric forms or as mixtures thereof. The activities of the stereoisomeric forms of a single compound may be different.

The compounds of sub-group C of formula I in which $R^4$ and $R^5$ both represent hydrogen may be prepared by a process in which a carbonyl compound of the formula:

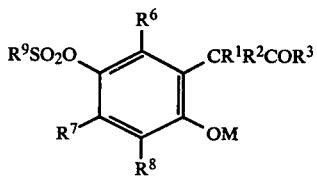

(wherein $R^1$, $R^2$, $R^3$, $R^6$, $R^7$, $R^8$ and $R^9$ are as defined hereinbefore and M represents an alkali-metal) is reduced, followed by acidification, to give the desired compound of formula I.

The reduction may be effected in any appropriate manner for reducing carbonyl groups without affecting the other groups in the molecule. Preferably, sodium borohydride is employed as the reducing agent.

The alkali-metal which M represents is preferably sodium or potassium.

The acidification may be effected by means of a mineral acid, e.g. hydrochloric acid.

The carbonyl compounds of formula II wherein $R^9$ represents alkylamino or dialkylamino are themselves novel compounds and this invention provides them per se.

The compounds of formula II may be prepared by a process in which a 2-hydroxy-benzo-furanyl sulphonate of the formula:

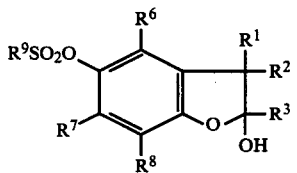

(wherein $R^1$, $R^2$, $R^3$, $R^6$, $R^7$, $R^8$ and $R^9$ are as defined hereinbefore) is treated with an alkali-metal hydroxide to give the desired compound of formula II.

The compounds of formula III are either known compounds or may be prepared from known compounds by techniques which will be familiar to those skilled in organic synthesis.

The compounds of sub-group C of formula I in which one of $R^4$ and $R^5$ is other than hydrogen or both of $R^4$ and $R^5$ are identical and other than hydrogen may be prepared from the corresponding compounds where $R^4$ and $R^5$ both represent hydrogen by reaction with one or two moles, as appropriate, of a halide of formula $R^4$Hal (where Hal represents halogen, e.g. bromine, and $R^4$ is as defined hereinbefore). Alternatively, where $R^4$ and/or $R^5$ in the desired compound represents carboxylic acyl, an anhydride of formula $R^4OR^4$ (where $R^4$ represents carboxylic acyl) may be employed instead of the halide. Alternatively, where $R^4$ and/or $R^5$ in the desired compound represents a group $C(=O)R^{10}$ where $R^{10}$ represents alkylamino or arylamino, an alkyl or aryl isocyanate, as appropriate, may be employed instead of the halide.

The compounds of sub-group C of formula I in which $R^4$ and $R^5$ are different may be prepared from the corresponding compounds where $R^4$ and $R^5$ both represent hydrogen by reaction with an appropriate amount of a halide, anhydride or alkyl or aryl isocyanate as above to give the corresponding compound wherein $R^5$ is hydrogen and $R^4$ is other than hydrogen, followed by reaction of the formed compound with an appropriate amount of a different halide, anhydride or alkyl or aryl isocyanate to give the corresponding compound where $R^4$ and $R^5$ are different and are both other than hydrogen.

The compounds of sub-group B of formula I may be prepared by a process in which a compound of sub-group C of formula I wherein $R^4$ and $R^5$ both represent hydrogen is reacted with a dihalide of formula Hal-Z-Hal (where Z is as defined hereinbefore, and Hal represents e.g. chlorine) in the presence of a base if necessary or desired to give the corresponding compound of sub-group B of formula I.

The reaction is desirably carried out in an appropriate solvent or suspension medium, other than a dialkylamide, e.g. an aromatic hydrocarbon, e.g. toluene.

Alternatively, where Z represents a group $—CR^{12}R^{13}—$ as defined hereinbefore, the dihalide may be replaced by a dialkoxy compound of formula $R^{15}O-ZOR^{15}$ (where $R^{15}$ represents an alkyl group, especially of 1–6 carbon atoms) in the presence of an acid catalyst, e.g. p-toluenesulphonic acid.

The compounds of sub-group A of formula I may be prepared by a process in which a compound of sub-group C of formula I wherein $R^4$ and $R^5$ both represent hydrogen is cyclised and dehydrated to give the desired compound.

The cyclisation and dehydration may conveniently be effected by means of a suitable dehydrating agent, for example phosphorus pentoxide or dicyclohexylcarbodiimide or, more preferably, a Vilsmeier reagent, for example of the formula:

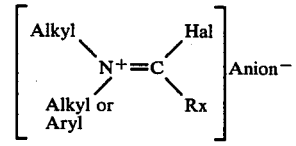

(where Rx represents hydrogen or alkyl, and Hal represents chlorine or bromine) to give the corresponding compound of sub-group A of formula I.

The Vilsmeier reagent, wherein Hal preferably represents chlorine, Rx preferably represents hydrogen, and each alkyl preferably represents methyl may be generated in situ by the reaction of a thionyl, phosphoryl or carbonyl chloride or bromide and a dialkylamide. It is preferred to employ thionyl chloride and dimethylformamide. The anion in the Vilsmeier reagent may be any suitable anion, for example $Cl^-$ or $Br^-$.

As will be apparent to those skilled in synthetic organic chemistry, the dehydration may be effected in several ways, e.g. by replacement of the group $R^4$ by a good leaving group, e.g. a halogen atom, followed by elimination of that group with the hydrogen atom which $R^5$ represents. Such processes are all encompassed by the term 'dehydration' as used herein.

The compounds of sub-group A of formula I may alternatively be prepared by a process in which a compound of sub-group B of formula I is heated in an appropriate dialkylamide solvent medium in the presence of an ionic salt to give the desired compound of sub-group A.

The solvent medium is desirably dimethylformamide.

The ionic salt is conveniently an alkali-metal salt, e.g. a halide, for example a chloride. Specifically preferred is sodium chloride.

The compounds of sub-group A of formula I may alternatively be prepared by a process in which a 5-hydroxybenzofuranyl compound of the formula:

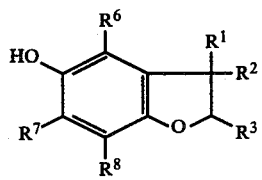

(VI)

(wherein $R^1$, $R^2$, $R^3$, $R^6$, $R^7$ and $R^8$ are as defined hereinbefore) is reacted with a sulphonyl halide of the formula $R^9SO_2Hal$ (where Hal represents a halogen atom) or an anhydride of the formula $(R^9SO_2)_2O$, $R^9$ being as defined hereinbefore, to give the desired compound of formula I.

The reaction is desirably effected in the presence of an organic base, for example an amine such as triethylamine.

The 5-hydroxybenzofuranyl compounds of formula VI may themselves be prepared by a multi-step process schematically represented as follows:

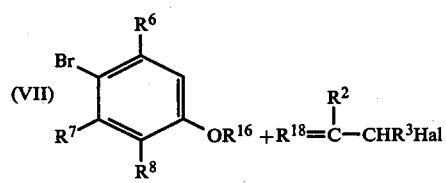

(VII) (VIII)

Step (a)

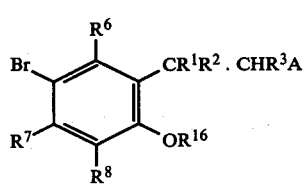

(IX)

Step (b)

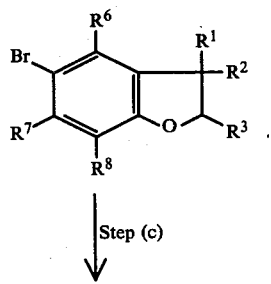

(X)

Step (c)

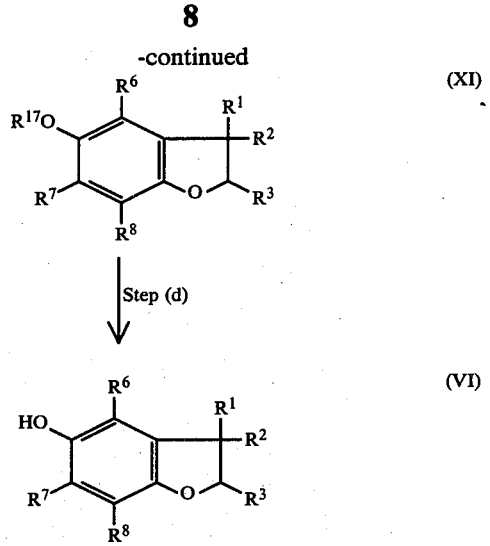

(XI)

Step (d)

(VI)

In the above scheme, $R^1$, $R^2$, $R^3$, $R^6$, $R^7$ and $R^8$ are as defined hereinbefore, $R^{16}$ and $R^{17}$ represent lower (i.e. C 1 to 6) alkyl groups, $R^{18}$ represents a divalent group formed by the removal of an alpha-hydrogen atom from a group $R^1$, and Hal represents a halogen atom (e.g. chlorine).

Step (d) is conveniently effected by dealkylating the compound of formula XI, preferably using as the dealkylating agent a salt of a mercaptan, in an appropriate solvent medium which is preferably of high boiling point, e.g. dimethylformamide.

Step (c) is conveniently effected by means of an alkoxide (suitably an alkali-metal alkoxide, especially of 1 to 6 carbon atoms), in the presence of a suitable catalyst, e.g. a transition metal salt, for example a copper or nickel salt, especially cuprous iodide. Generally the alkanol employed to generate the alkoxide acts as solvent medium for the reaction. Other solvents, e.g. dimethylformamide or xylene, may additionally be employed e.g. in order to raise the boiling point thereof.

Step (b) is a combined dealkylation and cyclisation. It is conveniently effected by heating the compound of formula IX with a mild dealkylating agent, e.g. a pyridine salt such as pyridine hydrochloride.

Step (a) is an alkylation reaction which is conveniently effected by reacting the compounds of formulae VII and VIII in the presence of an acid.

The compounds of formulae X, XI and VI are themselves novel compounds, with the exception of 3,3-dimethylbenzofuran-5-ol, and this invention provides them per se, together with processes for their preparation as described hereinbefore.

This invention extends, naturally, to the compounds of formula I whenever prepared by a process as described hereinbefore.

In a further aspect, this invention provides a method of combating weeds at a locus infested or liable to be infested with them, which method comprises applying to the locus at which they are growing an effective amount of one or more compounds of formula I.

The present compounds are normally employed in the form of compositions, which can be prepared by admixing the ingredients. Usually the compositions are initially produced in the form of concentrates, e.g. containing 0.5–85%, preferably 10 to 50%, by weight of the present compounds, and these are diluted with water or hydrocarbon, usually water, for application, generally such that the concentration of the compound is 0.05–5%. Percentages and parts in this specification are by weight unless otherwise indicated.

The compositions normally contain a surface active agent and/or a carrier.

The carrier may be a liquid, e.g. water (e.g. water used to dilute a concentrate for application). If water is employed as carrier in a concentrate, an organic solvent may also be present as carrier, though this is not usually employed. A surface active agent may advantageously be present.

The carrier may be a solid, which may be finely divided. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be a modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant e.g. a polyhalogenated alkane such as dichlorodifluoromethane, and suitably also with a solvent.

A flowable suspension concentrate may be formed by grinding the compound with water, a wetting agent and a suspending agent.

Thus the present composition can for example be solid (e.g. dust or granules) and contain a solid carrier, or liquid (e.g. an emulsifiable concentrate) and contain a liquid carrier which may for example be a ketone or a hydrocarbon which boils within the range 130°–270° C.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with fatty alcohol ethoxylates or salts of such esters, fatty alcohol sulphates such as sodium dodecyl sulphate, ethoxylated fatty alcohol sulphates, ethoxylated alkylphenol sulphates, lignin sulphonates, petroleum sulphonates, alkylaryl sulphonates such as alkyl-benzene sulphonates or lower alkyl-naphthalene sulphonates, salts of sulphonated naphthalene-formaldehyde condensates, salts of sulphonated phenol-formaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise non-ionic agents, for example condensation products of fatty acid esters, fatty alcohols, fatty acid amides or alkyl- substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyne-4,7-diol, or ethoxylated acetylenic glycols.

The surface active agents may also comprise cationic agents, for example alkyl- and/or aryl-substituted quaternary ammonium compounds such as cetyl trimethyl ammonium bromide, or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, salts of sulphonated phenol-fomaldehyde condensates, sodium oleolyl N-methyltauride, dialkyl sulphosuccinates, alkyl phenol ethoxylates, and fatty alkyl ethoxylates.

The present active compounds, particularly those specifically identified hereinbefore, and especially 2,3-dihydro-3,3-dimethylbenzofuran-5-yl ethanesulphonate, anesulphonate, methanesulphonate, 2-methyl-1-propanesulphonate, or 2-propanesulphonate, or 4-hydroxy-3-(2-hydroxy-1,1-dimethylethyl)phenyl ethanesulphonate or methanesulphonate, may be admixed with another pesticide, e.g. herbicide, insecticide or fungicide, or with a plant growth regulant or with a fertilizer. Particular advantages are obtained with mixtures with a second herbicide, e.g. one herbicide applied before planting or before emergence of a crop and the other herbicide applied after emergence of the crop.

The second herbicide employed in admixture or sequentially with the compounds of the present invention may be, for example, a substituted benzofuran herbicide, a phenoxyaliphatic acid, substituted urea, triazine, phenol, nitrile, bipyridylium compound, substituted benzoic acid, halogenated aliphatic acid, carbamate, thiocarbamate, chloroacetamide, diazine, arsenic compound or other herbicidal compound. In respect of selective herbicidal compositions for post-emergence use, the second herbicide is preferably a substituted phenoxyaliphatic acid; in respect of selective herbicidal compositions for pre-emergence use, the second herbicide is preferably a substituted benzofuran, a substituted urea or triazine.

The substituted benzofuran herbicide is preferably a compound of the formula:

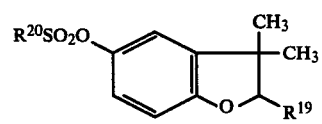

where $R^{19}$ represents alkoxy (especially ethoxy, propoxy or isopropoxy), and $R^{20}$ represents alkyl (especially methyl) or a group $R^{21}R^{22}N-$ where $R^{21}$ and $R^{22}$, which may be the same or different, each represent hydrogen, alkyl (especially methyl) or carboxylic acyl (especially acetyl).

A particularly preferred substituted benzofuranyl compound for admixture with the compounds of the present invention, especially with those specifically identified herein, is
2-ethoxy-2,3-dihydro-3,3-dimethylbenzofuran-5-yl methanesulphonate (common name ethofumesate).

The phenoxyaliphatic acid generally comprises alkyl and/or halogen substituted phenoxyaliphatic acids and their salts, for example alkali metal, amine and alkanolamine salts, and functional derivatives for example esters and amides. These compounds may be of activity such that they are recognised as commercial herbicides, or may be of only slight herbicidal activity.

The substituted urea generally comprises an N-phenyl-N',N'-dialkyl urea, e.g. 3-(3,4-dichlorophenyl)-1,1-dimethyl urea. The triazine herbicide generally comprises a 2-amino-4-alkyl- or n-propyl-amino-6-methylthio-s-triazine,

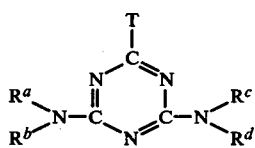

where T is a halogen or a group —OR$^e$ or —SR$^e$ where R$^e$ is an alkyl group, and R$^a$, R$^b$, R$^c$ and R$^d$ are hydrogen or alkyl.

Specific compounds with which the compounds of the present invention, especially those specifically identified herein, may be admixed are as follows, all common names being as set out in the Pesticide Manual, 4th edition, issued by the British Crop Protection Council:

alachlor, allidochlor, ametryne, aminotriazole (ATA), ancymidol, asulam, atrazine, aziprotryne, barban, benazolin, benfluralin, bensulide, bentazon, benthiocarb, bentranil, benzadox, benzoylprop-ethyl, benzthiazuron, bifenox, bromacil, bromofenoxim, bromoxynil, bromoxynil octanoate, brompyrazone, butachlor, buturon, butylate, carbetamide, chinonamid, chloramben, chloranocryl, chlorobromuron, chlorbufam, chlorfenac, chlorfenprop-methyl, chlorflurecol-methyl, chlormequat, chloroxuron, chlorphonium, chlorpropham, chlorthal-dimethyl, chlorthiamid, chlortoluron, credazine, cyanazine, cycloate, cycluron, cyprazine, 2,4-D, dalapon, dalapon sodium, daminozide, 2,4-DB, delachlor, desmedipham, desmetryne, diallate, dicamba, dichlobenil, dichlorprop, dimethametryn, difenzoquat, difenzoquat ethylsulphate, dimexan, dinitramine, dinoseb, dinoseb acetate, dinoterb, dinoterb acetate, diphenamid, dipropetryn, diquat, diuron, DNOC, DSMA, endothal, EPTC, erbon, ethiolate, EXD, fenoprop, fenuron, flamprop-isopropyl, fluometuron, fluorodifen, flumezin, flurecol-butyl, glyphosate, hexaflurate, ioxynil, ioxynil octanoate, isonoruron, isopropalin, isoproturon, karbutilate, lenacil, linuron, MCPA, MCPB, mecoprop, medinoterb acetate, merphos, methabenzthiazuron, methazole, methoprotryne, metobromuron, metoxuron, metribuzin, molinate, monalide, monolinuron, monuron, monuron-TCA, MSMA, napropamide, naptalam, neburon, nitralin, nitrofen, norflurazon, noruron, oryzalin, paraquat, pebulate, pentanochlor, phenmedipham, phenmedipham-ethyl, phenobenzuron, picloram, piperophos, profluralin, prometon, prometryne, propachlor, propanil, propazine, propham, propyzamide, pyrazon, secbumeton, siduron, simazine, simetryne, sulfallate, swep, 2,4,5-T, 2,3,6-TBA, TCA, terbacil, terbucarb, terbumeton, terbuthylazine, terbutryne, thiafluron, triallate, trietazine, trifluralin, and vernolate, N-(α,α,-dimethylbenzyl)-N'-p-tolylurea, 3,4,5-tribromo-N,N-dimethylpyrazole-1-acetamide (U 27267), N-methyl-N-cyclohexyldithio-N'-o-fluorophenyl urea, N-benzoyl-N-(3,4-dichlorophenyl)-N',N'-dimethyl urea, ethyl N,N-diisobutylthiolcarbamate, 4-(methylsulphonyl)-2,6-dinitro-N,N-dipropylaniline, 5(6)-chloro-2-isopropylbenzimidazole, [illegible], sodium cis-3-chloroacrylate, 4,5,[illegible]-tanamide, n-propyl ethyl-n-but[illegible]

dichloropropionanilide, N-cyclooctyl-N',N'-dimethylurea, butyl m-chlorophenylcarbamate, 2-chloro-N-(1,3-dioxolan-2-ylmethyl)-2',6'-dimethylacetanilide, tetrahydrofurfuryl isothiocyanate, N-chloroacetyl-N-(2,6-diethylphenyl)-glycine isopropyl ester, N-chloroacetyl-N-(2-methyl-6-ethylphenyl)-glycine isopropyl ester, (1methylethyl)O-methyl-O-(4-methyl-2-nitrophenyl)-phosphoramidothioate, 1,1-dimethylhexahydropyridazinum bromide, dimethylpiperidinium chloride, 1-[2-(2,4-dichlorophenyl)-1,3-dioxolan-2-methyl]imidazole, 3'-(trifluoromethyl)-phthalanilic acid, 3,6-dichloropropicolinic acid, benzyl 3,5-dichloro-2,6-difluoro-4-pyridyl ether, ethyl N-(2,4-dichlorophenyl)-N-(trifluoromethanesulphonyl)-carbamate, N-(p-chlorophenyl)-N-(trifluoromethanesulphonyl)-carbamate, N-(p-chlorophenyl)-3,4,5,6-tetrahydrophthalimide, tributyl[(5-chloro-2-thienyl)-methyl]phosphonium chloride, N-pyrrolidinosuccinamic acid, methyl-3,6-dichloro-o-anisate, ethyl 5-(4-chlorophenyl)-2-H-tetrazol-2-yl acetate, 2-(4-ethylamino-6-methylthio-s-triazin-2-yl)-amino-2-methylpropionitrile, 3-cyclohexyl-6-dimethylamino-1-methyl-1,3,5-triazine-2,4-(1H,3H)-dione, 1-(N-ethyl-N-propylcarbamoyl)-3-propyl-sulphonyl-1H-1,2,4-triazole, N-ethyl-N-(2-methyl-2-propenyl)-2,6-dinitro-4-(trifluoromethyl)-benzenamine, 2-ethyl-6-methyl-N-(1'-methyl-2'-methoxyethyl)-chloro-acetanilide, 2-(3-chlorophenoxy)-propionic acid, N-n-propyl-N-cyclopropylmethyl-4-trifluoromethyl-2,6-dinitro-aniline, N-benzyl-N-isopropyl-3,5-dimethylbenzamide, N-phenyldiethanolamine-bis(2-methoxy-3,6-dichlorobenzoate), [(3,5,6-trichloro-2-pyridinyl)oxy]-acetic acid, 3,3a-dihydro-2-(p-methoxyphenyl)-8H-pyrazolo-5,1-a-isoindol-8-one, r-2-ethyl-5-methyl-c-5-(2-methylbenzyloxy)-1,3-dioxane, 3-(1-N-ethoxyamino)-propyliden-6-ethyl-3,4-dihydro-2H-pyran-2,4-dione, N-(5-n-butylsulphonyl-1,3,4-thiadiazolyl)-N,N'-dimethyl urea, 1,1-dimethyl-3-(m-chloro-p-trifluoromethoxyphenyl)-urea, 2',6'-dimethyl-N-(2-methoxyethyl)-2-chloroacetanilide, 1-(α,α-dimethylbenzyl)-3-methyl-3-phenyl urea, 1-(o-fluorophenyl)-3-methyl-5-iminohydantoin, N-methyl-N-2-chlorocyclohexylthio-N'-(2-fluorophenyl) urea, 1-(3,4-dichlorophenyl)-3-methyl-3-(1-formyloxy-2,2,2-trichloroethyl)-urea, N-methyl-N-cyclohexyldithio-N'-o-fluorophenyl urea, N-carboxymethoxymethyl-2,6-diethyl-chloroacetanilide, 6-t-butyl-4,5-dihydro-3-isopropylpyridino-[4,5-c]isothiazol-4-one, 6-t-butyl-4,5-dihydro-3-isopropylpyrimidino-[5,4-d]-isoxazol-4-one, O-(5-chloro-1-isopropyl-1,2,4-triazol-3-yl) O,O-diethylphosphorothioate, 2,4-dichlorophenyl 3-methoxy-4-nitrophenyl ether, 2-ethyl-5-methyl-5-(2-methylbenzyloxy)-1,3-dioxan, N-(1-ethylpropyl)-2,6-dinitro-3,4-xylidine, hexafluoroacetone trihydrate, methyl tetrachloro-N-methoxy-N-methylterephthalamate, S,S,S-tributyl phosphorotrithioate, N-sec-butyl-2,6-dinitro-3,4-xylidine, N,N-dimethyl-2-(3,4,5-tribomo-1-pyrazolyl)-propionamide,α-(2,2,2-trichloroethyl)-styrene, 2-isopropyl-5-methyl-5-(2-[illegible]

bonyloxymethyl)-2',6'-diethyl-acetanilide, O-(isopropylsulphamoyl)-N-(but-1-yn-3-yl)-glycollanilide, ethyleneglycol bis-(trichloroacetate), hexachloroacetone, potassium cyanate, sodium chlorate, sodium metaborate, trichlorobenzyl chloride, undecylenic acid, N-(1-ethylpropyl)-3,4-dimethyl-2,6-dinitrobenzeneamine, tris(2-methoxyethoxy)-2'-chloroethylsilane, N-[2,4-dimethyl-5[[(trifluoromethyl)-sulphonyl]-amino]-phenyl]-acetamide, 6-t-butyl-4-isobutylideneamino-3-methylthio-1,2,4-triazin-5-(4H)-one, S-(4-methoxybenzyl-N,N-diethylcarbamothioate, 2-chloro-1-(3-ethoxy-4-nitrophenoxy)-4-trifluoromethylbenzene, 3-(3-chloro-4-trifluoromethoxyphenyl)-1,1-dimethyl urea, N-isobutyl-2-oxoimidazolidine-1-carboxamide, O-ethyl O-(3-methyl-6-nitrophenyl)-N-sec-butylphosphorthioamidate, 2,6-dichlorobenzyl (2,2-dimethyl-4-ethyldioxolan-4-yl)methyl ether, 3',5'-dinitro-4-(di-n-propylamino)-acetophenone, N-chloroacetyl-N-(2,6-diethylphenyl) glycine ethyl ester, 2,3:4,6-di-O-isopropylidene-2-keto-L-gulonate, 1-m-trifluoromethylphenyl-4-dimethylamino-5-chloropyridazone, 4-amio-3-methyl-6-phenyl-1,2,4-triazin-5-(4H)-one, N-(2-methoxy-1-methylethyl)-2'-ethyl-6'-methyl-2-chloroacetanilide, O-(N-phenylcarbamoyl)-propanone oxime, N-(4-methyl-3-(trifluoromethylsulphonylamino)phenyl)acetamide, 2,2,3,3-tetrafluoropropionic acid, O-methyl O-(4-methyl-2-nitrophenyl) (1-methylethyl)phosphoramidothioate, N-benzyl-N-isopropyl-3,5-dimethylbenzamide, 2-chloro-6-(2-cyano-1-methyl-ethylamino)-4-cyclopropylamino-s-triazine, 2,2-dimethyl-N-benzyl-N-isopropylpropionamide, 3-[5-(1,1-dimethylethyl)-1,3,4-thiadiazol-2-yl]-4-hydroxy-1-methyl-2-imidazolidinone, N-(3-chloro-4-ethoxyphenyl)-N',N'-dimethylurea, 1-methyl-4-phenylpyridinium chloride, N-[5-(2-chloro-1,1-dimethylethyl)-1,3,4-thiadiazol-2-yl]cyclopropane carboxamide, 4-t-butyl-N-s-butyl-2,6-dinitroaniline, 1,1'-di(diethylcarbamoylmethyl)-4,4'-bipyridylium dichloride, 2-t-butyl-4-(2-t-butyl-4-(3,3-dimethylureido)-phenyl)-1,3,4-oxadiazlin-5-one, 2',6'-dimethyl-N-(2-methoxyethyl)-2-chloroacetanilide, N-ethyl-N-propyl-3-(propylsulphonyl)- 1H-1,2,4-triazole-1-carboxamide, tris-(2-methoxyethyl)-2'-chloroethylsilane, N-ethyl-N-(2-methyl-2-propenyl)-2,6-dinitro-4-(trifluoromethyl)aniline, N-(2-chloroethyl)-2,6-dinitro-N-propyl-4-(trifluoromethyl)aniline, methyl N-benzoyl-N-(3-chloro-4-fluorophenyl)-2-aminopropionate, 2,4-dichloro-6-fluorophenyl 4-nitrophenyl ether, N-3-(1',1',2',2'-tetrafluoroethoxy)phenyl-N',N'-dimethylurea, 1-methyl-3-phenyl-5-[3-(trifluoromethyl)phenyl]-4-(1-H)-pyridinone, 2-amino-4-isopropylamino-6-chloropyrimidine, 6-t-butyl-4-isobutylideneamino-3-methylthio-1,2,4-triazin-5-(4H)-one, α-(4-chlorophenyl)-α-(1-methylethyl)-5-pyrimidinemethanol, 2-(2,4,5-trichlorophenoxy)ethanol, 2-chloroethyl-tris(methoxy)silane +α,ω-bis(2-chloroethyl)-α,α,ω-tetramethoxypoly[(2-chloroethyl)-methoxy]siloxane, O-ethyl O-(3-methyl-6-nitrophenyl) N-s-butylphosphorothioamidate, N-(2'-methoxy-1'-methylethyl)-2'-ethyl-6'-methyl-2-chloro-acetanilide, N-(2-methyl-2-propenyl)-2,6-dinitro-N-propyl-4-(trifluoromethyl)aniline, N-(1-phenyl-5-bromo-6-oxopyridazin-4-yl) oxamic acid sodium salt, 1,1,1-trifluoro-N-[2-methyl-4-(phenylsulphonyl)phenyl]methane sulphonamide, 3-ethoxycarbonylaminophenyl N-phenylcarbamate, ammonium ethyl carbamoylphosphonate, 1-allyl-1-tetrahydrogeranylpiperidinium bromide, N-((4-(dipropylamino)-3,5-dinitrophenyl)sulphonyl)-S,S-dimethylsulphilimine, 2-chloro-N-(1-methyl-2-propynyl)acetanilide, N-(5-butylsulphonyl-1,3,4-thiadiazol-2-yl)-N,N'-dimethylurea, 1,3-dimethyl-1-(5-dimethyl-sulphamoyl-1,3,4-thiadiazol-2-yl)urea, 1-(5-ethylsulphonyl-1,3,4-thiadiazol-2-yl)-1,3-dimethylurea, 1-(5-t-butyl-1,3,4-thiadiazol-2-yl)-1,3-dimethylurea, N-(butoxymethyl)-2-chloro-N-(2-(1,1-dimethylethyl)-6-methylphenyl)acetamide, 3-(3-chloro-4-chlorodifluoromethylthiophenyl)-1,1-dimethylurea, [(3,5,6-trichloro-2-pyridinyl)oxy]acetic acid, 2-[4-(4-trifluoromethylphenoxy)-phenoxy)]propionic acid methyl ester, and 3-cyclohexyl-6-(dimethyl-amino)-1-methyl-s-triazine-2,4-(1H,3H)-dione.

The invention also provides a two-container pack in which one or more compounds of formula I are provided in a first container and one or more further pesticides, plant growth regulants or fertilizers are provided in a second container, especially in relative proportions as described hereinafter. Desirably, the two-container pack bears or contains instructions, either separate or in conjunction with one of the containers, for mixing the contents of the containers or separately applying the contents thereof.

The ratio by weight of the compound(s) of the present invention to the second herbicide may vary over a wide range according to the particular compounds employed and the intended use. In general, however, the ratio by weight of the compound(s) of the present invention to the second herbicidal component will be from 10:1 to 1:15, more preferably from 5:1 to 1:5, and especially from 3:1 to 1:3.

The compounds of the present invention may, if desired, be employed in admixture with non-phytotoxic oils.

The compounds of the present invention are of herbicidal activity, and may be applied to plants, the soil, land or aquatic areas. They are of especial use as selective herbicides in crops, e.g. cotton ryegrass, safflower, sorghum, millets, sunflowers, tobacco, or a food crop such as cereals, sugar beet, peas, beans (e.g. navy beans, soya beans and field beans), carrots, peanuts, maize, rice and potatoes. They may be applied pre- or post-planting of the crop, and may be employed post-emergence or preferably pre-emergence. When used in cereals, they are preferably applied with one or more plant-growth hormones.

The compounds of formula I are preferably applied in an amount in total of from 0.1 to 20 kg/ha, more preferably 1 to 10 kg/ha, especially 2.5 to 8 kg/ha.

The invention will now be further described, though only by way of illustration, in the following Examples, in which all 'parts' are by weight.

EXAMPLE 1

4-Hydroxy-3-(2-hydroxy-1,1-dimethylethyl)phenyl methanesulphonate 2,3-Dihydro-2-hydroxy-3,3-dimethylbenzofuran-5-yl methane sulphonate (129 parts) was added to a solution of sodium hydroxide (120 parts) in water (1200 parts) and methanol (320 parts). Sodium borohydride (19 parts) was added portionwise with vigorous stirring at 15°–20° C. The mixture was stirred for three hours, then acidified with hydrochloric acid and filtered to give 4-hydroxy-3-(2-hydroxy-1,1-dimethylethyl)phenyl methanesulphonate (117 parts, 90% yield). Recrystallisation from 1,2-dichloroethane gave the pure product, melting point 122°–124° C.

Analysis:

Found: C, 50.94; H, 5.95; S, 12.05% $C_{11}H_{16}O_5S$ requires: C, 50.75; H, 6.20; S, 12.32%

EXAMPLE 2

The following compound was prepared by a method analogous to that of Example 1 but starting with the corresponding ethanesulphonate: 4-hydroxy-3-(2-hydroxy-1,1-dimethylethyl)phenyl ethanesulphonate, mp 127°–129° C. Its structure was confirmed by elemental analysis and IR and NMR spectra.

EXAMPLE 3

4-Acetoxy-3-(2-acetoxy-1,1-dimethylethyl)phenyl methanesulphonate

The product of Example 1 (d10 parts) was boiled under reflux with acetic anhydride (50 parts) for six hours. The excess anhydride was then evaporated off under reduced pressure and the residue treated with water. The product was extracted into ether and the ether extracts were washed with aqueous sodium bicarbonate solution and with water and dried over magnesium sulphate. The ether was then evaporated off to give 4-acetoxy-3-(2-acetoxy-1,1-dimethylethyl)phenyl methanesulphonate (11.6 parts, 88% yield) as an orange oil which solidified on standing to a pink solid, melting point 49°–51° C.
Analysis:
Found: C, 52.42; H, 5.97; S, 9.21% $C_{15}H_{20}O_7S$ requires: C, 52.31; H, 5.85; S, 9.31%

EXAMPLE 4

4Isobutyryloxy-3-(2-isobutyryloxy-1,1-dimethylethyl)-phenyl methanesulphonate Isobutyryl chloride (11.7 parts) was added dropwise with stirring at 5°–10° C. to a solution of the product of Example 1 (13 parts) and triethylamine (11.2 parts) in acetonitrile (80 parts). The mixture was stirred for three hours, then added to water (500 parts). The product was extracted into ether and the ether extracts were washed with dilute sodium hydroxide solution and with water and dried over magnesium sulphate. The ether was then evaporated off to give 4-isobutyryloxy-3-(2-isobutyryloxy-1,1-dimethylethyl)phenyl methanesulphonate (13.7 parts, 69% yield) as a yellow oil.
Analysis:
Found: C, 57.00; H, 6.97; S, 7.71% $C_{19}H_{28}O_7S$ requires: C, 56.98; H, 7.05; S, 8.01%

EXAMPLE 5

4-Methylcarbamoyloxy-3-(2-methylcarbamoyloxy-1,1-dimethylethyl) phenyl methanesulphonate Methyl isocyanate (68 parts) and triethylamine (2 parts) were added to a solution of the product of Example 1 (130 parts) in acetonitrile (400 parts). The mixture was kept for 20 hours at room temperature and then filtered. The filtrate was added to water (3000 parts) and the product isolated by ether extraction, washing and drying. The ether was evaporated off to give 4-methylcarbamoyloxy-3-(2-methylcarbamoyloxy-1,1-dimethylethyl)phenyl methanesulphonate (58 parts, 31% yield) as a colourless glass-like solid.

EXAMPLES 6–7

The following compounds were prepared by analogous methods to that described in Example 1. Structures were confirmed by their spectra and elemental analysis.

6. 4-hydroxy-3-(1-(hydroxymethyl)cyclopentyl)-phenyl methanesulphonate, melting point 131°–133° C.
7. 4-hydroxy-3-(1-hydroxymethyl)cyclohexyl)phenyl methanesulphonate, melting point 119°–122° C.

EXAMPLES 8–17

The following compounds were prepared by analogous methods to that described in Example 4. Structures were confirmed by their spectra and elemental analysis.

8. 4-chloroacetyloxy-3-(2-chloroacetyloxy-1,1-dimethylethyl)phenyl methanesulphonate, low melting solid.
9. 4-pentanoyloxy-3-(2-pentanoyloxy-1,1-dimethylethyl)phenyl methanesulphonate, orange liquid.
10. 4-benzoyloxy-3-(2-benzoyloxy-1,1-dimethylethyl)-phenyl methanesulphonate, melting point 98°–100° C.
11. 4-(ethoxycarbonyloxy)-3-(2-(ethoxycarbonyloxy)-1,1-dimethylethyl)phenyl methanesulphonate, melting point 69°–70° C.
12. 4-(4-chloro-2-butynyloxycarbonyloxy)-3-(2-(4-chloro-2-butynyloxycarbonyloxy)-1,1-dimethylethyl)-phenyl methanesulphonate,
13. 4-(2-choroethoxycarbonyloxy)-3(2-(2-chloroethoxycarbonyloxy)-1,1-dimethylethyl)phenyl methanesulphonate, viscous yellow liquid.
14. 4-methanesulphonyloxy-3-(2-methanesulphonyloxy-1,1-dimethylethyl)phenyl methanesulphonate, melting point 82°–84° C.
15. 4-(methoxycarbonyloxy)-3-(2-(methoxycarbonyloxy)1,1-dimethylethyl)phenyl methanesulphonate, melting point 76°–77° C.
16. 4-(trichloroacetyloxy)-3-(2-(trichloroacetyloxy)-1,1-dimethylethyl)phenyl methanesulphonate, viscous red-brown liquid.
17. 4-crotonyloxy-3-(2-crotonyloxy-1,1-dimethylethyl)-phenyl methanesulphonate, melting point <30° C.

EXAMPLE 18

3-(2-Benzoyloxy-1,1-dimethyl-ethyl)-4-hydroxyphenyl methanesulphonate

Benzoyl chloride (5.6g) in diethyl ether (50 ml) was added dropwise with vigorous stirring to a solution of 3-(2-hydroxy-1,1-dimethylethyl)-4-hydroxyphenyl methanesulphonate in aqueous sodium hydroxide solution (1.6g in 100 ml water). The mixture was stirred for three hours at room temperature, then separated, and the ether solution washed with dilute sodium hydroxide solution followed by water. Drying over magnesium sulphate and running down gave 4.5g of an oil. Crystallization from ethanol gave 0.7g of 3-(2-benzoyloxy-1,1-dimethyl-ethyl)-4-benzoyloxyphenyl methanesulphonate, m.p. 100°–101° C. Removal of the solvent from the mother liquors gave 2.5g of 3-(2-benzoyloxy-1,1-dimethyl-ethyl)-4-hydroxyphenyl methanesulphonate as a viscous oil.
Analysis:
$C_{18}H_{20}O_6S$ required: C, 59.32; H, 5.53 S, 8.80%
Found: C, 59.61; H, 5.34 S, 8.90%

EXAMPLE 19

The following compound was prepared by a method analogous to that of Example 5: 4-(phenylcarbamoyloxy)-3-(2-(phenylcarbamoyloxy-1,1-dimethylethyl)phenyl methanesulphonate, mp 59°–62° C.

EXAMPLE 20

4,5-Dihydro-5,5-dimethyl-2-oxido-1,3,2-benzodioxathiepin-7-yl methanesulphonate

Thionyl chloride (12 parts) was added dropwise at room temperature to a suspension of 4-hydroxy-3-(2-hydroxy-1,1-dimethylethyl)phenyl methanesulphonate (5 parts) (from Example 1) in toluene (50 parts). The mixture was gently warmed to 50° C. when reaction commenced, then maintained at this temperature for 15 minutes. The temperature was then raised to boiling point and the mixture boiled under reflux for 2 hours. The solvent was then evaporated off under reduced pressure to give crude 4,5-dihydro-5,5-dimethyl-2-oxido-1,3,2-benzodioxathiepin-7-yl methanesulphonate (5.2 parts, 90% yield). Recrystallization from ethanol gave the pure product (2.4 parts), melting point 96°–98° C.

Analysis:

Found: C, 43.51; H, 5.07; S, 21.16% $C_{11}H_{14}O_6S_2$ requires: C, 43.12; H, 4.61; S, 20.93%

EXAMPLE 21

4,5-Dihydro-2,2,5,5-tetramethyl-1,3-benzodioxepin-7-yl methanesulphonate

A mixture of 4-hydroxy-3-(2-hydroxy-1,1-dimethylethyl)phenyl methylsulphonate (10 parts) (from Example 1), 2,2-dimethoxypropane (17 parts) and p-toluenesulphonic acid (0.1 parts) was heated in toluene (90 parts) with distillation of low boiling fraction and slow addition of further 2,2-dimethoxypropane (17 parts) for 1 hour. The resulting solution was cooled, washed with aqueous sodium hydroxide solution and with water, dried over magnesium sulphate and the solvent evaporated off under reduced pressure. The crude product was distilled yielding 9 parts of 4,5-dihydro-2,2,5,5-tetramethyl-1,3-benzodioxepin-7-yl methanesulphonate, boiling point 130°–142° C./0.2 mm Hg. Recrystallisation from aqueous ethanol gave the pure product (4.8 parts), melting point 65°–67° C.

Analysis:

Found: C, 55.89; H, 6.72; S, 10.44% $C_{14}H_{20}O_5S$ require: C, 55.98; H, 6.71; S, 10.67%

EXAMPLE 22

4,5-Dihydro-2-methoxy-5,5-dimethyl-1,3-benzodioxepin-7-yl methanesulphonate

4-Hydroxy-3-(2-hydroxy-1,1-dimethylethyl)phenyl methanesulphonate (10.4 parts) (from Example 1) was reacted with trimethyl orthoformate (127 parts) in the presence of p-toluenesulphonic acid (0.05 parts) as in Example 20 to produce 4,5-dihydro-2-methoxy-5,5-dimethyl-1,3-benzodioxepin-7-yl methanesulphonate (9.5 parts, 79% yield) as a colourless oil.

Analysis:

Found: C, 52.00; H, 6.05; S, 10.21% $C_{13}H_{18}O_6S$ requires: C, 51.64; H, 6.00; S, 10.60%

EXAMPLES 23–35

The following compounds were prepared by analogous methods to those described in Examples 21 and 22. Structures were confirmed by their spectra and elemental analysis.

23. 2-ethyl-4,5-dihydro-2,5,5-trimethyl-1,3-benzodioxepin-7-yl methanesulphonate, m.p. 75°–76° C.
24. 2,2-diethyl-4,5-dihydro-5,5-dimethyl-1,3-benzodioxepin-7-yl methanesulphonate, viscous yellow liquid.
25. 4,5-dihydro-2-isopropyl-2,5,5-trimethyl-1,3-benzodioxepin-7-yl methanesulphonate, m.p. 92°–93° C.
26. 4,5-dihydro-5,5-dimethyl-1,3-benzodioxepin-7-yl methanesulphonate, m.p. 69°–71° C.
27. 4,5-dihydro-2,5,5-trimethyl-1,3-benzodioxepin-7-yl methanesulphonate, m.p. 44°–45° C.
28. 4,5-dihydro-5,5-dimethyl-2-phenyl-1,3-benzodioxepin-7-yl methanesulphonate, m.p. 86°–87° C.
29. 4,5-dihydro-2,5,5-trimethyl-2-phenyl-1,3-benzodioxepin-7-yl methanesulphonate, m.p. 85°–86° C.
30. 4,5-dihydro-5,5-dimethylspiro[1,3-benzodioxepin-2,1'-cyclohexan]-7-yl methanesulphonate, m.p. 82°–83° C.
31. 4,5-dihydro-5,5-dimethylspiro[1,3-benzodioxepin-2,1'-cyclopentan]-7-yl methanesulphonate, m.p. 59°–61° C.
32. 2-chloromethyl-4,5-dihydro-2,5,5-trimethyl-1,3-benzodioxepin-7-yl methanesulphonate, m.p. 85°–87° C.
33. 2-bromomethyl-4,5-dihydro-5,5-dimethyl-1,3-benzodioxepin-7-yl methanesulphonate, m.p. 68°–69° C.
34. 2-ethoxy-4,5-dihydro-5,5-dimethyl-1,3-benzodioxepin-7-yl methanesulphonate, light brown viscous liquid.
35. 2-ethyl-4,5-dihydro-2-methoxy-5,5-dimethyl-1,3-benzodioxepin-7-yl methanesulphonate, m.p. 59°–61° C.

EXAMPLE 36

2-Ethoxy-4,5-dihydro-5,5-dimethyl-2-oxo-1,3,2-benzodioxaphosphepin-7-yl methanesulphonate 4-Hydroxy-3-(2-hydroxy-1,1-dimethylethyl)phenyl methanesulphonate (10g) from Example 1 was suspended in acetonitrile (100 ml) and triethylamine (8g) was added. The mixture was cooled in ice, and ethyl phosphorodichloridate (6.9g) was added dropwise with vigorous stirring. Stirring was continued for 6 hours prior to the addition of dichloromethane (200 ml), after which the solution was washed with water, dilute sodium hydroxide solution and water again, dried over magnesium sulphate and run down. The crude product was recrystallised from toluene, yielding 6.0g of the desired product, melting point 113°–115° C.

Analysis:

Found: C, 44.57 H, 5.47% $C_{13}H_{19}O_7PS$ requires: C, 44.35 H, 5.70%

EXAMPLE 37

2,3-Dihydro-3,3-dimethylbenzofuran-5-yl methanesulphonate (a) 2-Methylallyl chloride (108 parts) was added dropwise to a mixture of 4-bromoanisole (240 parts) and a concentrated sulphuric acid (20 parts) over a period of 2 hours at a temperature of 25°–35° C. Stirring was continued for 5 hours and the mixture was then kept for 24 hours at room temperature. Ether (400 parts) was then added and the resulting solution washed with water, aqueous sodium bicarbonate solution and water again. After drying with sodium sulphate and evaporating off the solvent the brown oil which remained was distilled yielding 4-bromo-2-(2-chloro-1,1-dimethylethyl)anisole (118 parts), boiling point 106°–120°/0.4 mm Hg. Recrystallisation from petroleum ether (b.p. 80°–100° C.) gave the pure product (98 parts), melting point 86°–88° C.

This product was heated with pyridine hydrochloride (235 parts) at 200° C. with stirring for 1 hour and then poured into iced dilute hydrochloric acid. Isolation through ether and distillation gave a crude product (50 parts), b.p. 135°–140° C./31 mm Hg. Purification gave pure 5-bromo-2,3-dihydro-3,3-dimethylbenzofuran (35.7 parts), boiling point 65°–70° C./0.3 mm Hg.

A mixture of this product, cuprous iodide (6 parts) and dimethyl formamide (130 parts) was added to a stirred solution of sodium methoxide (34 parts) in methanol (110 parts) and the mixture boiled under reflux for 3 hours. Addition to water and ether extraction followed to evaporating off the solvent under reduced pressure gave an orange oil (27 parts). Distillation yielded 2,3-dihydro-5-methoxy-3,3-dimethylbenzofuran (19.8 parts, 71% yield), boiling point 137°–145° C./34 mm Hg.

A solution of ethanethiol (12.6 parts) in dimethyl formamide (60 parts) was added with stirring under nitrogen over a period of 20 minutes to a mixture of sodium hydride (6.6 parts of 80% dispersion in oil) and dry dimethyl formamide (60 parts) cooled to 0° C. After 10 minutes, a solution of 2,3-dihydro-5-methoxy-3,3-dimethylbenzofuran (18 parts) in dimethyl formamide (40 parts) was added and the mixture boiled under reflux in a nitrogen atmosphere for 3 hours. The mixture was then added to water and the aqueous phase washed with chloroform, acidified with hydrochloric acid and extracted into ether. The ether was evaporated off to yield, 2,3-dihydro-3,3-dimethyl-benzofuran-5-ol (5.4 parts) as a brown oil.

Methanesulphonyl chloride (4.12 parts) was added dropwise to a stirred solution of the above product and triethylamine (3.66 parts) in ether (35 parts), keeping the temperature below 10° C. After stirring for 3 hours at room temperature, the mixture was filtered and diluted with petroleum ether (b.p. 60°–80° C.). White crystals formed, which were filtered off and dried to give 2,3-dihydro-3,3-dimethylbenzofuran-5-yl methanesulphonate (4.8 parts), melting point 75°–77° C.
Analysis:
Found: C, 54.14; H, 5.99% $C_{11}H_{14}O_4S$ requires: C, 54.53; H, 5.82%

(b) A mixture of 4,5-dihydro-5,5-dimethyl-2-oxido-1,3,2-benzodioxathiepin-7-yl methanesulphonate (24 parts) (from Example 20) and sodium chloride (1 part) in dimethyl formamide (400 parts) was boiled under reflux for 3 hours. The mixture was then added to water and the product extracted with ether to give 2,3-dihydro-3,3-dimethylbenzofuran-5-yl methanesulphonate (16 parts, 84% yield), identical with the product of Example 37(a) above.

(c) Thionyl chloride (83 parts) was added dropwise with cooling to dimethyl formamide (260 parts). To this mixture was then added dropwise a solution of 4-hydroxy-3-(2-hydroxy-1,1-dimethylethyl)phenyl methanesulphonate (180 parts) (from Example 1) in dimethyl formamide (190 parts) with stirring at about 15° C. The mixture was then stirred for one hour at room temperature and for five hours at 100° C. Addition to water (2000 parts) caused precipitation of an off-white solid which was filtered off and recrystallised from aqueous ethanol to give 2,3-dihydro-3,3-dimethylbenzofuran-5-yl methanesulphonate (65.2 parts) identical with the product of Example 37(a) above.

EXAMPLE 38

2,3-Dihydro-3,3-dimethylbenzofuran-5-yl ethanesulphonate

Thionyl chloride (4.3g) was added dropwise to dimethylformamide (13 ml) maintained at about 5° C. To this was quickly added 4-hydroxy-3-(2-hydroxy-1,1-dimethylethyl)phenyl ethanesulphonate (9.5g) from Example 2 in dimethylformamide (13 ml). The reaction mixture was then heated to 100° C. and maintained at that temperature for 4–5 hours, after which it was cooled and poured into water (100 ml). The oil was extracted with diethyl ether, washed with water, dried over magnesium sulphate and evaporated down to give 6.2g of a brownish oil.
Analysis:
Found: C, 56.28 H, 6.47% $C_{12}H_{16}O_4S$ requires: C, 56.23 H, 6.29%

The same compound was also prepared by reacting 2,3-dihydro-3,3dimethyl-5-benzofuranol with ethanesulphonyl chloride in the presence of triethylamine in an analogous way to that described in Example 37(a).

EXAMPLES 39–49

The following compounds were prepared by analogous methods to that described in the final stage of Example 37(a), by reacting 2,3-dihydro-3,3-dimethyl-5-benzofuranol with the appropriate sulphonyl chloride in the presence of triethylamine: 39. 2,3-dihydro-3,3-dimethylbenzofuran-5-yl methylsulphamate, melting point 52°–54° C. 40. 2,3-dihydro-3,3-dimethylbenzofuran-5-yl 1-propanesulphonate, oil. 41. 2,3-dihydro-3,3-dimethylbenzofuran-5-yl 1-butanesulphonate, oil. 42. 2,3-dihydro-3,3-dimethylbenzofuran-5-yl p-toluenesulphonate, mp 103°–105° C. 43. 2,3-dihydro-3,3-dimethylbenzofuran-5-yl β-toluenesulphonate, mp 129°–131° C. 44. 2,3-dihydro-3,3-dimethylbenzofuran-5-yl 3-chloro-1-propanesulphonate, oil. 45. 2,3-dihydro-3,3-dimethylbenzofuran-5-yl 2-methyl-1-propanesulphonate, oil. 46. 2,3-dihydro-3,3-dimethylbenzofuran-5-yl 2-propanesulphonate, oil. 47. 2,3-dihydro-3,3-dimethylbenzofuran-5-yl cyclohexanesulphonate. 48. 2,3-dihydro-3,3-dimethylbenzofuran chloromethanesulphonate, oil. 49. 2,3-dihydro-3,3-dimethylbenzofuran 2-butanesulphonate, oil.

EXAMPLE 50

Spiro[benzofuran-3(2H),1'-cyclopentan]-5-yl methanesulphonate

The product of Example 6(6.7g) in dimethylformamide (20 ml) was added in portions to thionyl chloride in 5 ml of dimethylformamide with cooling to 20° C. The reactants were stirred at that temperature for 30 minutes and were then heated to 100° C. and maintained there for 5½ hours. The mixture was then poured into water and extracted into diethyl ether three times. The extracts were combined, washed with water, sodium bicarbonate solution and water twice more and were then dried over magnesium sulphate, filtered and evaporated down leaving an oil which was taken up in diethyl ether. It was then cooled in solid carbon dioxide/acetone to give a white solid which was filtered off to give 1.2g of product, mp 75°–77° C.

EXAMPLE 51

A 20% emulsifiable concentrate was prepared from the following:

| | |
|---|---|
| 2,3-dihydro-3,3-dimethylbenzofuran-5-yl methanesulphonate | 200g |
| 'Arylan CA' (70% alcoholic solution of calcium dodecylbenzenesulphonate) | 25g |
| 'Ethylan C40 AH' (condensation product of castor oil with 40 moles of ethylene oxide) | 25g |
| Isophorone (to 1 liter) | approx 750ml | surface application of 11.2 kg of compound per hectare cultivated to a depth of 5 cm. Seeds of pea (*Pisum sativum*), mustard (*Sinapis alba*), linseed (*Linum usitatissimum*), maize (*Zea mays*), oats (*Avena sativa*) and ryegrass (*Lolium sp.*) were then sown in the treated soil, one species to each pan, watered and kept in a controlled environment room (temperature 22° C., relative humidity 65–85%, 14 hours per day artificial illumination of 13000 lux) for 21 days.

The plants were then assessed visually for any growth regulatory or herbicidal effect, difference from untreated controls being assessed on a scale from 0 to 9 in which 0 signifies no effect and 9 signifies complete suppression. The results are listed below:

| Compound Product of Example No | Herbicidal Activity | | | | | |
|---|---|---|---|---|---|---|
| | Pea | Mustard | Linseed | Ryegrass | Oats | Maize |
| 1 | 7 | 9 | 8 | 9 | 9 | 8 |
| 2 | 7 | 9 | 8 | 9 | 9 | 9 |
| 3 | 5 | 7 | 8 | 8 | 9 | 8 |
| 4 | 5 | 7 | 8 | 8 | 9 | 8 |
| 6 | 3 | 9 | 9 | 9 | 9 | 8 |
| 7 | 1 | 3 | 5 | 8 | 8 | 2 |
| 8 | 2 | 4 | 6 | 5 | 8 | 3 |
| 9 | 6 | 8 | 9 | 9 | 9 | 9 |
| 11 | 3 | 8 | 7 | 9 | 9 | 5 |
| 13 | 2 | 6 | 6 | 8 | 9 | 6 |
| 15 | 4 | 6 | 8 | 8 | 8 | 4 |
| 16 | 3 | 7 | 8 | 8 | 8 | 5 |
| 17 | 5 | 9 | 8 | 9 | 9 | 7 |
| 18 | 6 | 8 | 8 | 8 | 9 | 9 |
| 20 | 6 | 9 | 9 | 9 | 9 | 9 |
| 21 | 5 | 6 | 9 | 8 | 8 | 9 |
| 22 | 3 | 6 | 8 | 7 | 9 | 9 |
| 23 | 4 | 6 | 9 | 9 | 9 | 9 |
| 24 | 6 | 8 | 8 | 8 | 9 | 7 |
| 25 | 4 | 8 | 8 | 8 | 9 | 8 |
| 29 | 4 | 7 | 8 | 7 | 9 | 6 |
| 30 | 1 | 4 | 6 | 4 | 9 | 1 |
| 31 | 7 | 9 | 9 | 9 | 9 | 9 |
| 34 | 7 | 8 | 8 | 9 | 9 | 9 |
| 35 | 6 | 8 | 9 | 9 | 9 | 9 |
| 37 | 7 | 9 | 8 | 7 | 9 | 9 |
| 38 | 7 | 8 | 8 | 9 | 9 | 9 |
| 39 | 6 | 9 | 7 | 9 | 8 | 7 |
| 40 | 5 | 6 | 6 | 9 | 8 | 8 |
| 45 | 4 | 9 | 7 | 9 | 9 | 9 |
| 46 | 6 | 9 | 8 | 9 | 9 | 9 |

EXAMPLE 52

A 50% wettable powder was prepared from the following:

| | by wt |
|---|---|
| 4-hydroxy-3-(1-(hydroxymethyl)cyclopentyl)phenyl methanesulphonate | 50% |
| 'Reax 45L' (combined wetting and dispersing agent based on lignin sulphonate) | 5% |
| China Clay | 45% |

EXAMPLES 53-54

Formulations equivalent to those of Examples 51 and 52 with the exception that the active ingredient employed was 2,3-dihydro-3,3-dimethylbenzofuran-5-yl ethanesulphonate were also prepared.

EXAMPLE A

The compounds listed below were formulated as an attaclay/sand dust and incorporated into John Innes No 1 potting compost at a rate of 26 parts per million weight/volume of compound to soil and placed in anodised aluminium pans, 20 cm long × 10 cm wide × 5 cm deep. This rate is approximately equivalent to a soil

EXAMPLE B

Pre-emergence

The compounds listed below formulated as: (I) an attaclay/sand dust and incorporated in John Innes I potting compost at a rate equivalent to 6.5 ppm weight/volume of active ingredient to soil and placed in anodised aluminium pans, 19 cm long × 9.5 cm wide × 5 cm high. This is approximately equivalent to a surface application of 2.8 kg active ingredient per hectare cultivated to a depth of 5 cm. Seeds of the species listed below were sown in the treated soil, one species per pan, watered and placed in a controlled environment room (22° C.; 65–86% R.H. and 14 hours artificial illumination at 1600 foot candles) for 21 days; (II) An aqueous suspension together with 1000 ppm of the wetting agent Lissapol NX. The surfaces of an additional set of pans with seeds already sown were then sprayed with 2.8 kg/ha in 450 liters/hectare. The plants were then visually assessed for any growth regulatory or herbicidal effects. All differences from an untreated control were scored on a scale from 0-100, where 0 signifies no effect and 100 signifies complete suppression. The results are summarised in the following table:

| Species | Example No | | | | | | | | | | | | | | | |
|---|---|---|---|---|---|---|---|---|---|---|---|---|---|---|---|---|
| | 20 | | 21 | | 22 | | 23 | | 24 | | 25 | | 28 | | 29 | |
| | I | II | I | II | I | II | I | II | I | II | I | II | I | II | I | II |
| Chickweed (*Stellaria media*) | 9 | 9 | 9 | 9 | 9 | 9 | 9 | 9 | 9 | 9 | 8 | 9 | 8 | 8 | 9 | 9 |
| Mustard (*Sinapis alba*) | 5 | 6 | 6 | 6 | 6 | 5 | 7 | 6 | 2 | 2 | 4 | 3 | 2 | 2 | 3 | 3 |
| Cotton (*Gossypium sp*) | 4 | 6 | 7 | 6 | 5 | 4 | 6 | 3 | 3 | 1 | 4 | 1 | 3 | 2 | 4 | 1 |
| Tomato (*Lycopersicon esculentum*) | 6 | 7 | 7 | 7 | 8 | 7 | 8 | 8 | 7 | 7 | 6 | 6 | 3 | 3 | 7 | 7 |
| Fathen (*Chenonpodium album*) | 7 | 9 | 8 | 9 | 8 | 9 | 8 | 9 | 8 | 9 | 7 | 9 | 6 | 8 | 8 | 8 |
| Carrot (*Daucus carota*) | 5 | 7 | 4 | 7 | 6 | 8 | 6 | 7 | 5 | 5 | 2 | 6 | 2 | 3 | 5 | 5 |
| Wheat (*Triticum aestivum*) | 9 | 8 | 9 | 8 | 9 | 8 | 9 | 6 | 8 | 7 | 8 | 6 | 8 | 5 | 9 | 8 |
| Barley (*Hordeum vulgare*) | 8 | 6 | 9 | 8 | 9 | 5 | 8 | 5 | 7 | 4 | 6 | 3 | 8 | 2 | 8 | 7 |
| Wild Oat (*Avena fatua*) | 6 | 7 | 7 | 9 | 8 | 7 | 8 | 7 | 7 | 6 | 6 | 8 | 6 | 2 | 8 | 5 |
| Blackgrass (*Alopecurus myosuroides*) | 8 | 9 | 8 | 8 | 7 | 6 | 6 | 5 | 6 | 4 | 3 | 2 | 4 | 3 | 8 | 7 |
| Barnyardgrass (*Echinochloa crus-galli*) | 6 | 6 | 8 | 7 | 8 | 7 | 6 | 2 | 4 | 7 | 3 | 4 | 1 | 1 | 8 | 6 |
| Crabgrass (*Digitaria sanguinalis*) | 9 | 9 | 9 | 9 | 9 | 9 | 9 | 9 | 8 | 9 | 5 | 8 | 5 | 6 | 9 | 9 |

| Species | Example No | | | | | | | | | | | | | | | |
|---|---|---|---|---|---|---|---|---|---|---|---|---|---|---|---|---|
| | 31 | | 34 | | 35 | | 37 | | 38 | | 40 | | 45 | | 46 | |
| | I | II | I | II | I | II | I | II | I | II | I | II | I | II | I | II |
| Chickweed (*Stellaria media*) | 9 | 8 | 8 | 9 | 9 | 9 | 9 | 9 | 9 | 9 | 9 | 9 | 8 | 9 | 9 | 9 |
| Mustard (*Sinapis alba*) | 6 | 4 | 4 | 3 | 5 | 3 | 8 | 9 | 7 | 6 | 5 | 6 | 2 | 0 | 7 | 7 |
| Cotton (*Gossypium sp*) | 5 | 4 | 4 | 2 | 6 | 4 | 8 | 6 | 4 | 3 | 0 | 2 | 2 | 0 | 4 | 3 |
| Tomato (*Lycopersicon esculentum*) | 6 | 7 | 6 | 6 | 7 | 6 | 8 | 8 | 8 | 8 | 9 | 9 | 7 | 7 | 8 | 8 |
| Fathen (*Chenonpodium album*) | 7 | 9 | 7 | 8 | 8 | 8 | 8 | 9 | 9 | 9 | 8 | 9 | 0 | 7 | 7 | 8 |
| Carrot (*Daucus carota*) | 4 | 6 | 4 | 6 | 5 | 6 | 4 | 5 | 1 | 3 | 3 | 4 | 0 | 0 | 2 | 2 |
| Wheat (*Triticum aestivum*) | 9 | 9 | 9 | 9 | 9 | 8 | 9 | 8 | 9 | 9 | 6 | 7 | 6 | 3 | 8 | 8 |
| Barley (*Hordeum vulgare*) | 9 | 8 | 9 | 8 | 9 | 7 | 9 | 9 | 9 | 9 | 4 | 4 | 4 | 3 | 8 | 8 |
| Wild Oat (*Avena fatua*) | 8 | 8 | 8 | 8 | 8 | 9 | 7 | 9 | 7 | 8 | 0 | 6 | 3 | 8 | 8 | 9 |
| Blackgrass (*Alopecurus myosuroides*) | 9 | 8 | 9 | 9 | 9 | 9 | 9 | 9 | 8 | 9 | 6 | 9 | 6 | 9 | 7 | 8 |
| Barnyardgrass (*Echinochloa crus-galli*) | 9 | 8 | 9 | 8 | 9 | 8 | 8 | 9 | 9 | 9 | 4 | 9 | 8 | 8 | 8 | 9 |
| Crabgrass (*Digitaria sanguinalis*) | 9 | 9 | 9 | 9 | 9 | 9 | 8 | 9 | 9 | 9 | 7 | 9 | 7 | 9 | 9 | 9 |

We claim:

1. A sulphonate of the formula:

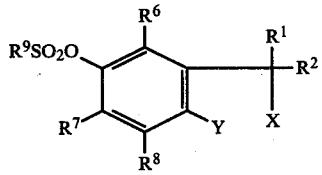

wherein X and Y together represent a group —CH-$R^3$—O—, the free oxygen atom of which is attached to the benzene ring; $R^1$, $R^2$ and $R^3$, which may be the same or different, each represent hydrogen or C 1 to 6 alkyl; $R^6$, $R^7$ and $R^8$, which may be the same or different, each represent hydrogen, C 1 to 6 alkyl, halogen, cyano, C 2 to 6 carboxylic acyl, or C 1 to 4 alkoxy; and $R^9$ represents C 1 to 6 alkyl, phenyl or C 7 to 10 phenylalkyl (each of which may be unsubstituted or substituted by one or more chlorine or bromine atoms, C 1 to 4 alkyl groups, C 1 to 4 alkoxy groups or nitro groups), C 5 to 7 cycloalkyl, C 1 to 4 alkylamino, or dialkylamino wherein each alkyl moiety has from 1 to 4 carbon atoms.

2. A compound according to claim 1 wherein $R^1$ represents methyl or ethyl.

3. A compound according to claim 1 wherein $R^2$ represents methyl or ethyl.

4. A compound according to claim 1 wherein $R^3$, $R^6$, $R^7$ and $R^8$ each represent hydrogen.

5. A compound according to claim 1 wherein $R^9$ represents methyl, ethyl, n-propyl, isopropyl, n-butyl, isobutyl or s-butyl (each of which is unsubstituted or substituted by a chlorine or bromine atom), phenyl or benzyl (each of which is unsubstituted or substituted by one or more chlorine or bromine atoms or methyl, methoxy or nitro groups), cyclopentyl, cyclohexyl, methylamino, ethylamino or dimethylamino.

6. A compound according to claim 1 wherein $R^1$ represents methyl or ethyl, $R^3$, $R^6$, $R^7$ and $R^8$ each represent hydrogen, and $R^9$ represents methyl, ethyl, n-propyl, isopropyl, n-butyl, isobutyl, s-butyl, chloromethyl, 3-chloropropyl, phenyl, benzyl, p-tolyl, cyclopentyl, cyclohexyl, methylamino, ethylamino or dimethylamino.

7. A compound according to claim 1 which is:
2,3-dihydro-3,3-dimethylbenzofuran-5-yl methanesulphonate;
2,3-dihydro-3,3-dimethylbenzofuran-5-yl ethanesulphonate;
2,3-dihydro-3,3-dimethylbenzofuran-5-yl 1-propanesulphonate;
2,3-dihydro-3,3-dimethylbenzofuran-5-yl 1-butanesulphonate;
2,3-dihydro-3,3-dimethylbenzofuran-5-yl 2-propanesulphonate;
2,3-dihydro-3,3-dimethylbenzofuran-5-yl 2-butanesulphonate;
2,3-dihydro-3,3-dimethylbenzofuran-5-yl 2-methyl-1-propanesulphonate;
2,3-dihydro-3,3-dimethylbenzofuran-5-yl chloromethanesulphonate;
2,3-dihydro-3,3-dimethylbenzofuran-5-yl 3-chloro-1-propanesulphonate;
2,3-dihydro-3,3-dimethylbenzofuran-5-yl cyclohexanesulphonate;
2,3-dihydro-3,3-dimethylbenzofuran-5-yl p-toluenesulphonate;
2,3-dihydro-3,3-dimethylbenzofuran-5-yl 2-toluenesulphonate; or
2,3-dihydro-3,3-dimethylbenzofuran-5-yl methylsulphamate.

8. A method of combating weeds at a locus infested or liable to infestation therewith, which comprises applying to said locus an effective amount of one or more compounds according to claim 1.

9. A herbicidal composition which comprises from 0.5 to 85% by weight of one or more compounds according to claim 1 in association with a suitable carrier and/or surface active agent.